(12) United States Patent
Kleinfeld et al.

(10) Patent No.: US 6,999,173 B2
(45) Date of Patent: Feb. 14, 2006

(54) METHOD AND APPARATUS FOR RATIO FLUOROMETRY

(75) Inventors: Alan M. Kleinfeld, La Jolla, CA (US); Pavel V. Vodkin, Sunnyvale, CA (US)

(73) Assignee: FFA Sciences LLC, San Diego, CA (US)

( * ) Notice: Subject to any disclaimer, the term of this patent is extended or adjusted under 35 U.S.C. 154(b) by 76 days.

(21) Appl. No.: 10/670,958

(22) Filed: Sep. 25, 2003

(65) Prior Publication Data

US 2005/0068534 A1 Mar. 31, 2005

(51) Int. Cl.
*G01N 21/25* (2006.01)

(52) U.S. Cl. ............... 356/417; 422/82.02; 356/317

(58) Field of Classification Search ............ 356/417, 356/436, 317, 318; 422/82.08; 436/172; 250/459.1
See application file for complete search history.

(56) References Cited

U.S. PATENT DOCUMENTS

| | | | | |
|---|---|---|---|---|
| 4,580,059 A | * | 4/1986 | Wolfbeis et al. | 436/172 |
| 4,833,332 A | * | 5/1989 | Robertson et al. | 356/417 |
| 5,470,714 A | * | 11/1995 | Kleinfeld | 435/7.8 |
| 6,563,585 B1 | * | 5/2003 | Rao et al. | 356/436 |

OTHER PUBLICATIONS

Grynkiewicz, Grzegorz, et al., *The Journal of Biological Chemistry*, vol. 260, No. 6, Issue of Mar. 25, pp. 3440-3450, 1985, "A New Generation of $Ca^{2+}$ Indicators with Greatly Improved Fluorescence Properties."

Richieri, Gary V., et al., *The Journal of Biological Chemistry*, vol. 267, No. 33, Issue of Nov. 25, pp. 23495-23501, 1992, "A Fluorescently Labeled Intestinal Fatty Acid Binding Protein."

Richieri, Gary V., et al., *The Journal of Biological Chemistry*, vol. 271, No. 19, Issue of May 10, pp. 11291-11300, 1996, "Kinetics of Fatty Acid Interactions with Fatty Acid Binding Proteins from Adipocyte, Heart and Intestine."

Richieri, Gary V., et al., *The Journal of Biological Chemistry*, vol. 271, No. 49, Issue of Dec. 6, pp. 31068-31074, 1996, "Thermodynamic and Kinetic Properties of Fatty Acid Interactions with Rat Liver Fatty Acid-binding Protein."

* cited by examiner

*Primary Examiner*—Layla G. Lauchman
(74) *Attorney, Agent, or Firm*—Knobbe Martens Olson & Bear LLP

(57) ABSTRACT

A method and apparatus for determining the concentration of molecules or atoms by measuring the ratio of two fluorescence signals. A sample having fluorescent molecules is exposed to radiation or excitation energy from a first source, which can be a broadband light source. The fluorescence of the sample is detected at two different wavelengths. The concentration of specific molecules or atoms within the sample is determined using the ratio of the two fluorescence signals. Fluorescent molecules can be bound to a human serum or plasma sample to allow determination of the concentration of unbound free fatty acids in the sample.

80 Claims, 6 Drawing Sheets

METHOD AND APPARATUS FOR RATIO FLUOROMETRY

BACKGROUND OF THE INVENTION

1. Field of the Invention

The invention relates to determining concentrations of molecules or atoms. More particularly, the invention relates to determining such concentrations using the ratio of two fluorescence signals.

2. Description of the Related Art

Concentrations of atoms or molecules in samples, such as biological samples, often need to be determined in clinical medicine and basic science applications. Some molecules can be detected by determining a level of fluorescence exhibited by the molecule when subjected to excitation. Other target molecules or atoms can be detected by binding different fluorescent molecules to the target molecules or atoms and detecting the fluorescence exhibited by the fluorescent molecules that are bound to the target molecule or atoms. The excitation energy is partially absorbed by the fluorescent molecules and is emitted, typically, as energy at a predetermined wavelength.

The fluorescence from a sample can be measured using a spectrometer. Typical spectrometers are large and expensive laboratory equipment that are usually only found in research facilities. Additionally, the results from the spectrometer need to be subjected to further signal processing in order to determine the concentration of a particular molecule or atom in the sample. More direct, inexpensive, and accessible instruments and methods are desired for detecting the concentrations of molecules and atoms in samples.

SUMMARY OF THE INVENTION

A method and apparatus is disclosed for determining the concentration of molecules or atoms by measuring the ratio of two fluorescence signals. A sample having fluorescent molecules is exposed to radiation or excitation energy from a first source, which can be a broadband light source, a filtered light source, or a narrowband light source. The fluorescence of the sample is detected at two different wavelengths. The ratio of the two detected values is calculated and the concentration of specific molecules or atoms within the sample is determined using the ratio of the two fluorescence signals. In one embodiment, fluorescent molecules can be used to allow determination of the concentration of unbound free fatty acids in a human serum, plasma, or whole blood sample.

BRIEF DESCRIPTION OF THE DRAWINGS

The above-described aspects and other aspects, features and advantages of the invention will be apparent upon review of the following detailed description and the accompanying drawings. In the drawings like reference characters identify identical or functionally equivalent elements.

DETAILED DESCRIPTION OF THE PREFERRED EMBODIMENT

A method and apparatus of determining the concentrations of molecules in a sample using the ratio of fluorescence or other emissions from the sample are disclosed. The sample is excited with an excitation source and the emissions are detected using two or more detectors. A ratio based, at least in part, on the detected emissions is calculated. The concentration of a target molecule can then be determined based, at least in part, on the calculated ratio. Different embodiments and calculations are described in more detail below.

A number of different fluorescent molecules are known that undergo a change in fluorescence upon binding specific atoms or molecules, such as ligands. In a number of instances the change in fluorescence that these molecules exhibit reveals a fluorescence at one wavelength when unbound and a fluorescence at a different wavelength or a different polarization when bound. Other fluorescent molecules exhibit a change in characteristics that are not related to wavelength. Such changes in characteristics of the fluorescent molecules include, but are not limited to intensity, polarization, or time decay.

The ratio of two fluorescent signals can be used to determine the fraction of bound or unbound molecules, or targets such as ligands, in a sample. The fraction of bound or unbound molecules can be determined with a high degree of accuracy using this method. The ratio can be determined directly using a single fluorescent molecule when the molecule exhibits fluorescence at one wavelength when bound and exhibits fluorescence at another wavelength when unbound. If the fluorescent molecule exhibits a change in characteristics at a single wavelength when bound to a target, a second fluorescent molecule that emits a different wavelength can be used to determine the ratio. The second fluorescent molecule can be used as a reference fluorophore that does not exhibit a change in fluorescence in the presence of the target. The second fluorescent molecule used as the reference fluorophore does not substantially change emission characteristics in the presence of the target.

The use of this ratio technique to determine the concentration of atoms or molecules in fluids can be extremely useful in clinical medicine as well as basic science. For example, fluorescent molecules formed by attaching a fluorescent molecule to proteins that bind fatty acids can be used to determine the concentration of unbound free fatty acid in human fluids. This concentration has been found to indicate the presence or absence of cardiac ischemia.

Figure 1:
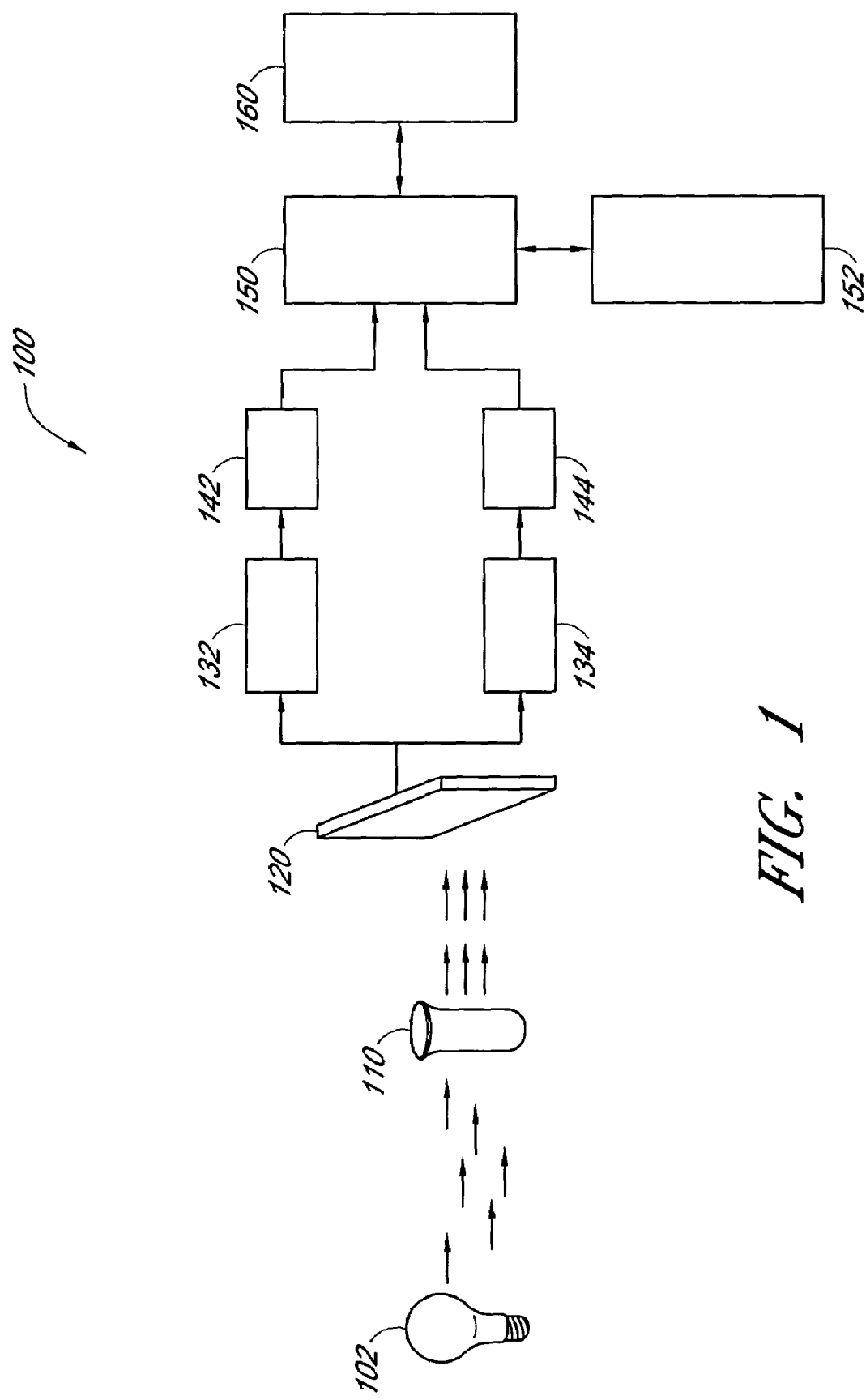
FIG. 1 is a functional block diagram of a ratio fluorometer.

FIG. 1 is a functional block diagram of a ratio fluorometer 100. The ratio fluorometer 100 can be configured to determine the concentration of unbound free fatty acids in human fluids.

The ratio fluorometer 100 includes a sample receptacle 110 that is used to hold a sample of the material that is to be measured by the ratio fluorometer 100. An excitation source 102 is used to excite or radiate the sample receptacle 110, and thus the sample. Some of the fluorescent molecules within the sample absorb energy from the excitation source 102. The fluorescent molecules in the sample receptacle 110 can then emit energy in the form of emitted light or some other emitted energy. The light or other radiated energy emitted from the fluorescent molecules is detected by a detector 120.

The output of the detector 120 is typically an electrical signal that corresponds to the energy emitted by the fluorescent molecules contained in the sample receptacle 110. The output of the detector 120 is provided to a first filter 132. The first filter 132 filters the output from the detector 120 to pass only the portion of the detected signal. The portion of the detected signal passed by the first filter 132 corresponds to first pass band. The first pass band can represent a predetermined frequency band or a predetermined span of wavelengths. The output of the first filter 132 is coupled to a first Analog to Digital Converter (ADC) 142. The first ADC 142 converts the electrical signal passed by the first filter 132 into a digital representation. The output of the first ADC 142 is coupled to a processor 150.

Similarly, the output of the detector 120 is coupled to a second filter 134 having a second pass band. The pass band of the second filter 134 is typically different from the pass band of the first filter 132. The output from the second filter 134 is coupled to a second ADC 144 that converts the output from the second filter 134 into a digital representation. The output of the second ADC 144 is coupled to the processor 150.

The processor determines the concentration of target molecules or atoms in the sample well 110, in part, by calculating a ratio of the outputs from the first and second ADCs, 142 and 144, respectively. The process of determining the concentration of molecules or atoms in the sample receptacle 110 will be discussed in more detail below.

The processor 150 can provide an output to a user interface 160 to allow results to be delivered to a user in a convenient format. The user interface 160 can include, but is not limited to, a display, readout, output port, and the like, or some other means for delivering a user output.

The ratio fluorometer 100 is not limited to the configuration shown in FIG. 1, but may be configured in a variety of ways depending, for example, on the material to be examined and design considerations. The elements of the ratio fluorometer can be rearranged to many different configurations. The ratio fluorometer 100 is shown in FIG. 1 with a digital implementation. However, digital electronics are not essential to the operation of the ratio fluorometer 100. As an alternative, the ratio fluorometer 100 can be implemented using analog electronics and an analog display, such as a meter, may be used to provide an ouptut For example, the excitation source 102 is shown as an illumination source, but can be chosen to be a particular excitation source 102. For example, the excitation source 102 can be a light source, a broadband light source, a narrow band light source, a coherent light source, a visible light source, an arc lamp, an infrared light source, an ultraviolet light source, an electromagnetic excitation source, an x-ray source, a filtered excitation source, a polarized excitation source, multiple excitation sources, and the like, or some other means for exciting the sample.

Additionally, the sample receptacle 110 can be, for example, a cuvette, a sample well, a microtiter well, a test tube, a gel plate, a drop target, and the like, or some other means for receiving a sample. The sample receptacle 110 can include a temperature sensor or the sample receptacle 110 may be mounted to a holder that includes a temperature sensor. The processor 150 may periodically read the temperature indicated by the temperature sensor and adjust a value, such as the concentration of unbound free fatty acids, based in part on the temperature.

The detector 120 can be, for example, a single detector, multiple detectors, a broadband detector, a narrow band detector, a radiation detector, a photomultiplier tube, a photodiode, an avalanche photodiode, an electromagnetic receiver, an image plate, a Charge Coupled Device (CCD), a CMOS detector, a camera, and the like, or some other means for detecting sample emissions.

Additionally, although the detector 120 typically detects an amplitude or intensity of a signal, the detector can detect, for example, an intensity, amplitude, polarization, power, energy, wavelength, bandwidth, and the like of the signal. Furthermore, detecting the fluorescence typically refers to detecting the intensity of the fluorescence but can refer to detecting, for example, the intensity, amplitude, polarization, power, energy, wavelength, bandwidth, and the like, of the fluorescence. For example, a single broadband detector can be used in conjunction with configurable filters and multiple measurements may be multiplexed using the single detector. In another example, a diffraction grating can be used in conjunction with a single detector and the position of the single detector may be positioned to align with a particular wavelength passing through the diffraction grating.

In one embodiment, the detector 120 can be a broadband detector and multiple measurements may be made with the same detector 120. A first measurement may be made using a first filter 132 and a second measurement may be made using a second filter 134. The first and second filters 132 and 134 may be positioned mechanically. Alternatively, a passband of the filter, for example 132, may be electronically controlled and the passband of the first filter 132 may be adjusted from a first passband to a second passband. The detector 120 may make a first measurement when the filter 132 is configured with the first passband. The detector 120 may make a second measurement when the filter 132 is configured with the second passband.

The filters 132 and 134 can be various types of filters and can be placed before or after the detector 120, depending on the type of filter. For example, optical filters may be placed before the detector 120 and electromagnetic filters may be placed following the detector 120. The filters 132 and 134 can be, for example, optical filters, colored glass filters, interference filters, diffraction filters, refraction filters, polarization filters, radiation filters, electromagnetic filters, cavities, waveguides, and the like, or some other means for filtering a signal. The filters 132 and 134 may have fixed passbands or may have variable passbands. Additionally, the filters 132 and 134 may have fixed bandwidths or may have variable bandwidths.

Similarly, the ADCs 142 and 144 can be various types of ADCs. For example, ADCs 142 and 144 can be a single ADC or can be multiple ADCs. Additionally, the ADCs 142 and 144 can be, for example, linear ADCs, logarithmic ADCs, sigma-delta ADCs, and the like, or some other means for generating a digital output.

Thus, it can be seen that there are many design choices that can be made depending on the desired configuration, the type of sample that is to be measured, and the fluorescent molecules or other emitting molecules that are found or included in the sample material.

Figure 2:
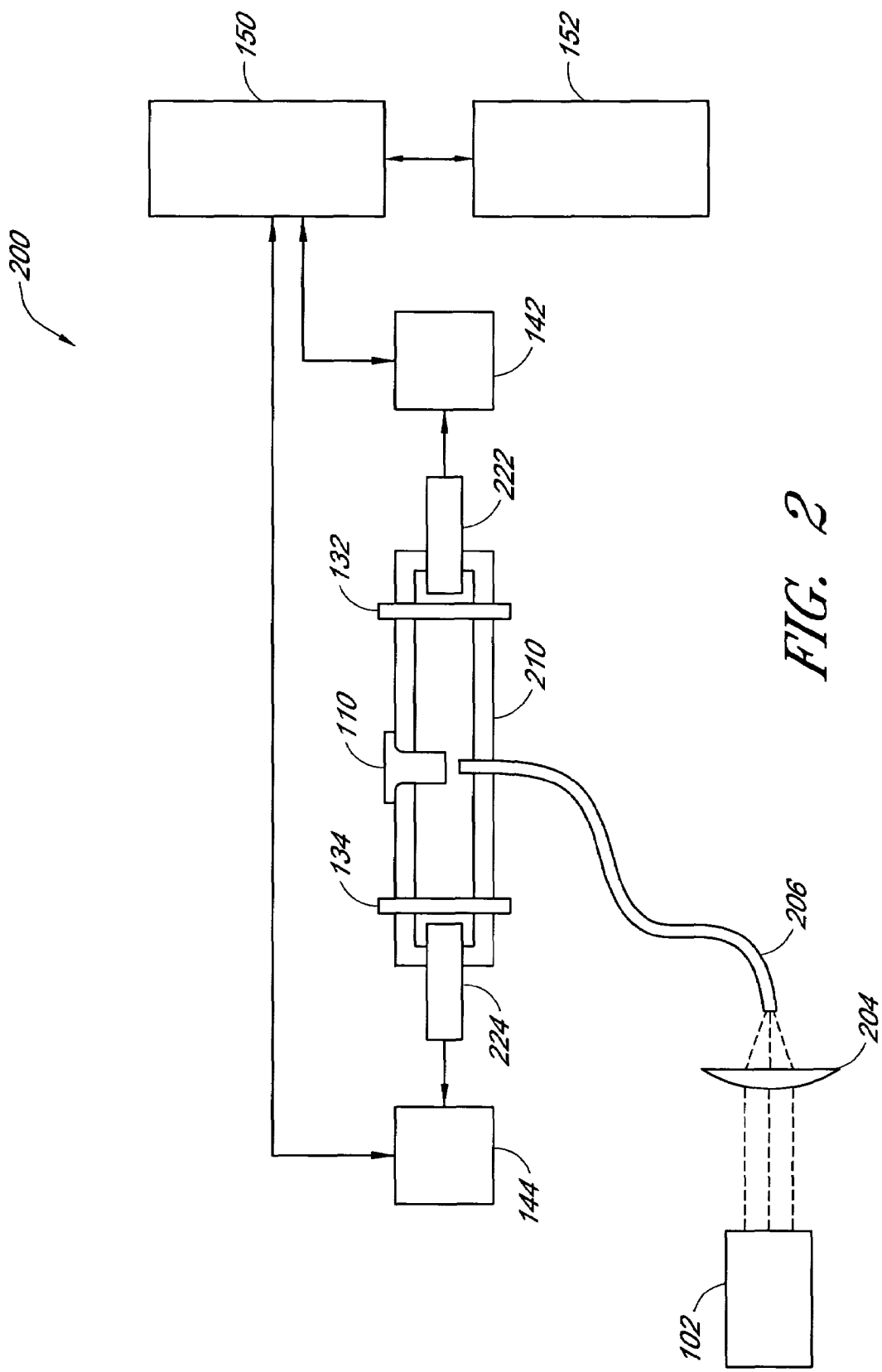
FIG. 2 is a functional block diagram of another embodiment of a ratio fluorometer.

FIG. 2 is a functional block diagram of an example of a ratio fluorometer 200 configured to determine the concentration of unbound free fatty acid in human fluids. Of course, as seen by the description of FIG. 1, the ratio fluorometer 200 is not limited to only determining a concentration of this analyte.

A xenon light source is the excitation source 102. A xenon light source is a nearly white light source that emits light over a broad spectrum. The excitation source 102 illuminates a lens 204 that focuses the light on a first, or input end of an optical fiber 206. The optical fiber 206 is a fiber optic cable or light pipe that allows light from the excitation source 102 to be routed to the sample receptacle 110.

In FIG. 2, the optical fiber extends through an opening or hole in a support structure 210. A section view of the support structure 210 is shown to enable elements contained within the support structure to be shown. The support structure 210 can be a tube, such as a square aluminum tube having approximately one inch sides. Of course, the ratio fluorometer 200 is not limited to particular dimensions and material of the support structure 210.

The second, or output side, of the optical fiber 206 is positioned near the sample receptacle 110. The second side of the optical fiber 206 is shown positioned underneath the sample receptacle 110 such that the sample receptacle 110 is illuminated from the bottom. However, the second end of the optical fiber 206 can be positioned through a hole in the side of the support structure 210 such that the sample receptacle 110 is illuminated from one side.

The sample receptacle 110 receives the sample to be tested and can be a cuvette such as a 10×10 mm cuvette. The sample receptacle 110 is typically transparent to both the illumination from the excitation source 102 as well as the desired fluorescence from the sample. The sample receptacle 110 need not be completely transparent, but any attenuation of the excitation or fluorescent signals should be relatively uniform over the surface of the sample receptacle 110.

A first filter 132 is positioned in the support structure 210 along one side of the sample receptacle 110. The first filter 132 is shown positioned in front of the first detector 222. The first filter 132 is positioned such that it is substantially orthogonal to the illumination from the excitation source 102. Where the excitation source 102 illuminates the sample receptacle 110 from one side, the first filter 132 can be positioned approximately 90 degrees from the illumination axis, such that the filter is orthogonal to the illumination from the excitation source 102. The first filter 132 is an optical band pass filter and can advantageously be an optical filter centered at 457 nm. The first filter 312 can advantageously have a bandwidth of 20 nm.

Light emitting from the sample receptacle 110 is filtered using the first filter 132 and then passed to a first detector 222. The first detector 222 can be a photomultiplier tube, such as a battery powered Hamamatsu photomultiplier tube. The detected output from the first detector 222 is coupled to a first ADC 142. The first ADC 142 digitizes the detected signal from the output of the first detector 222. The output from the first ADC 142 is coupled to a processor 150.

A second filter 134 is positioned on a side of the sample receptacle 110 opposite the first filter 132. The second filter 134 is also positioned substantially orthogonal to the illumination from the excitation source 102. The second filter 134 is an optical band pass filter centered at 550 nm and having a bandwidth of 20 mm.

The second filter 134 filters light emitting from the sample receptacle 110. Light passing through the second filter 134 is detected using the second detector 224. The second detector 224 can also be a photomultiplier tube, such as a battery powered Hamamatsu photomultiplier tube.

The detected output from the second detector 224 is converted to a digital representation using the second ADC 144. The output of the second ADC 144 is coupled to the processor. The processor 150 determines the concentration of unbound free fatty acids in the sample based in part on the ratio of the two detected signals. The processor 150 can be a processor within a computer, such as a personal computer.

The processor 150 can determine the concentration of unbound free fatty acids ($FFA_u$) in aqueous buffers and in human serum or plasma using the fluorescent molecule ADIFAB2 or ADIFAB. To determine $FFA_u$, fluorescent molecules are added to a sample. These reagents and suitable assay protocols are disclosed in U.S. Pat. Nos. 5,470,714 and 6,444,432, and U.S. application Ser. No. 10/243,565 publication no. 20030054412A1 and Ser. No. 10/128,101 publication no. 20030054412A1, the entire disclosures of which are incorporated herein by reference.

In general, the accuracy of the ratio fluorometer, for example 200, can be tested using one or more control solutions. Multiple control solutions having different concentrations of a desired molecule can be prepared and the concentrations measured using the ratio fluorometer 200. The accuracy of the ratio fluorometer 200 can be periodically verified using the control solutions. For $FFA_u$, the control solutions can comprise $FFA_u$ buffers. A control solution may contain a fatty acid mixed with albumin to produce a sample with a known $FFA_u$ concentration. A reagent, such as ADIFAB, may be added to a series of prepared control solutions with known concentrations to verify the accuracy of the instrument.

Alternatively, or in addition to using prepared control solutions, a solid or solution standard may be used to verify that the ratio fluorometer, for example 200, is properly functioning. A solid standard can include a fluorophore solid embedded within a solid matrix. A solution standard can include a fluorophore in a defined solution. It may be advantageous for the solution standard to include a well characterized, stable, fluorophore in a defined solution. For example, a solution standard can include quinine sulfate in 0.1 N sulfuric acid.

The solid or solution standard can be configured in the shape of, or using, a sample receptacle 110. The concentration measured by the ratio fluorometer 200 with the solid or solution standard can be compared against a predetermined range to indicate whether the instrument is properly functioning. Thus, proper functioning of the ratio fluorometer 200 can be verified initially, periodically, or if functionality of the instrument is in doubt. The use of a previously prepared solid or solution standard allows the functionality of the instrument to be determined without the need for preparing control solutions.

A verification test of the ratio fluorometer 200 was conducted using a controlled sample. Control samples of sodium oleate in complex with Bovine Serum Albumin (BSA) was prepared to generate defined concentrations of unbound free fatty acid. This sample was diluted approximately 100 fold in aqueous buffer and 2 ml of sample was added to a cuvette, which is used as the sample receptacle 110. The cuvette was placed in the ratio fluorometer 200 and intensities from both detectors 222 and 224 were sampled for 10 to 30 seconds. These intensities are the blank intensities. The blank intensities may be measured prior to adding the target sample into the sample well. Alternatively, blank intensities for a number of control samples may be measured and stored into memory for use with sample testing. The processor may then be configured to allow one of the stored blank intensity measurements to be recalled and used in the determination of the target concentration.

The cuvette was removed from the instrument and an amount of ADIFAB2 was added to yield a final concentration in the cuvette of 1 $\mu M$. Intensity measurements were repeated and the blank intensities at each wavelength were subtracted from the intensities with ADIFAB2 present.

The processor calculates a ratio (R) according to the formula:

$$R=(I(\lambda_1)-I(\lambda_1)\text{blank})/(I(\lambda_2)-I(\lambda_2)\text{blank}) \quad \text{eq(1)}$$

Where $\lambda_1$ and $\lambda_2$ refer to the two different detected emission wavelengths and $I(\lambda)$ represents the detected intensity at the wavelength. In the ratio fluorometer of FIG. 2, the detected emission wavelengths correspond to 550 nm and 457 nm. These emission wavelengths correspond to wavelengths of fluorescence of ADIFAB2.

A calibration factor is preferably applied to the ratio (R) to calibrate the ratio fluorometer 200 to produce accurate ratio calculations and thus, accurate determinations of concentrations.

The use of the calibration factor allows the ratio fluorometer 200 to generate accurate $\text{FFA}_u$ values by performing a single measurement of Ro, the ratio of the indicator molecule's intensities with zero fatty acid present. The principle that underlies this method is described below. The ratio of fluorescence intensities for a given fluorophore, observed by a dual detector system is:

$$R=f*r^{int} \quad \text{eq(2)}$$

In this equation $r^{int}=i(\lambda_1)/i(\lambda_2)$ and $i(\lambda)$ is the intrinsic fluorescence intensity of the fluorophore at wavelength $\lambda$ and f is a factor that depends on the relative efficiency, geometry, and amplification of the two detectors. The variables $\lambda_1$ and $\lambda_2$ may refer to the wavelengths of maximum fluorescent emissions for unbound and bound fluorescent moieties, respectively. Thus, in one embodiment, in the presence of target molecules in the sample, the signal at $\lambda_1$ will decrease and the signal at $\lambda_2$ will increase. The observed ratios for two different fluorometers designated A and B, are:

$$R(A)=f(A)*r^{int} \quad \text{eq(3)}$$

$$R(B)=f(B)*r^{int} \quad \text{eq(4)}$$

Therefore the R values for two different instruments are related as:

$$R(A)/R(B)=f(A)/f(B). \quad \text{eq(5)}$$

In particular, the R value in the presence of substantially zero $\text{FFA}_u$ is Ro. Determining the Ro values with the two instruments allows the determination of $f(A)/f(B)$, $$f(A)/f(B)=Ro(A)/Ro(B). \quad \text{eq(6)}$$

For example, instrument A can be the calibrating fluorometer, the one on which the binding constants, spectral parameters, and reference Ro value are determined. These are the parameters used in determining the concentration of $\text{FFA}_u$ as indicated in equation 8. Then, equation 5 can be solved for the value of R(B) to give the R values on instrument B.

$$R(B)=f(A)/f(B)*R(A). \quad \text{eq(7)}$$

If B is a two detector ratio fluorometer, such as the ratio fluorometer 200 of FIG. 2, the relative amplification of the two detectors can be adjusted so that f(B)=f(A). This is done by using a zero $\text{FFA}_u$ sample to set the amplification of B so that f(B)=f(A) and therefore Ro(B)=Ro(A). With B calibrated in this fashion, R values measured with B can be converted to $\text{FFA}_u$ with equation 8.

$$\text{FFA}_u=Z*(R-Ro)/(Rm-R) \quad \text{eq(8)}$$

Here Z is $K_d^{mix}*Q$ and Rm is the maximum value of the ratio. These three parameters are determined as described for the fluorescent molecule, for example ADIFAB or ADIFAB2. The three values are determined using the calibrating fluorometer, in this example fluorometer A. Fluorometer A is also used to determined the absolute value of Ro (Ro(A)) used in equation 8. Although in this example Ro is the ratio for zero $\text{FFA}_u$ concentration, it is apparent that the method can also be extended to ratios for non-zero $\text{FFA}_u$ concentrations.

Thus, more than one set of calibration factors can be predetermined using a calibrating fluorometer. The values for the sets of calibration factors can be stored in memory and accessed by the processor to allow accurate determinations of concentrations of various molecules or atoms. It is apparent that this method can be extended to atoms or molecules that are not fatty acids. For example, fluorescent molecules can be used to determine the concentration of calcium and magnesium ions by ratio fluorescence, and for these ions Ro is determined in the presence of Ethylene Glycol Tetra Acetic acid (EGTA) or Ethylene Diamine Tetra Acetic acid (EDTA), which are effective chelators of these ions and thereby are capable of producing an effectively zero concentration.

The ratio fluorometer 200 is also configured to minimize the potential effects of interference. There are two main forms of potential interference that can affect the ratio and thus the accuracy of the $\text{FFA}_u$ value determined using the ratio. The first interference source is emission from the sample being assayed with no fluorescent molecule added. This is termed the "blank" and represents fluorescence and scatter from the sample. The ratio is corrected for this contribution by subtraction of the blank intensities at each wavelength as described in equation 1.

The second type of interference is due to absorbance at the emission wavelengths by chromophores present in the sample in the absence of added fluorophores. For example, hemoglobin absorbs strongly for wavelengths between about 400 and 600 nm and is typically present in whole blood samples and often present in serum or plasma. Therefore the ratio fluorometer 200 is configured to minimize the effect of hemoglobin.

If the absorbance is different at each emission wavelength then the ratio is altered.

$$R_{altered}=R*10^{\Delta OD} \quad \text{eq(9)}$$

Here $\Delta OD$ is the optical density (OD) difference at the two emission wavelengths. The determination of $\Delta OD$ entails a measurement in addition to the fluorescence ratio.

Interference due to absorbance at the emission wavelengths can be corrected by examining an absorbance spectrum of the interference contributor. Then two bandwidths are chosen in the absorbance spectrum where the optical densities are equal. That is, the optical density centered about a first wavelength $OD(\lambda_1)$ is substantially equal to the optical density centered about a second wavelength $OD(\lambda_2)$. Advantageously, the two bandwidths in the absorbance spectrum are chosen to coincide with emission bandwidths for the fluorophore. The bandwidths chosen from examination of the absorbance spectrum may not, and typically do not, coincide with peak intensity bands of the fluorophore.

The ratio fluorometer 200 makes use of the characteristics of the hemoglobin absorbance spectrum in such a way so as to obtain $\Delta OD=0$ in equation 9. An examination of the absorbance spectrum of oxyhemoglobin reveals substantially equal absorbance at approximately 457 and 550 nm. Moreover, the slope of absorbance at 457 nm is negative and the intensity will be collected over a finite band width (for example 10 or 20 nm). The second emission bandwidth is thus chosen to be centered near 550 nm where the slope of absorbance is also negative. Thus, the average absorbances for finite bandwidths centered around 457 nm and 550 nm are virtually identical.

The ratio fluorometer 200 configuration having emission bandwidths chosen to minimize effects of hemoglobin absorbance was tested by measuring $FFA_u$ in a specimen of human serum in the presence of increasing concentrations of hemoglobin. The measurements were performed using the fluorophore ADIFAB2 and either a single detector fluorometer or a two detector ratio fluorometer. Results with either fluorometer reveal that $FFA_u$ determined by this method is substantially unaffected by hemoglobin over a wide range of hemoglobin concentrations.

Figure 3:
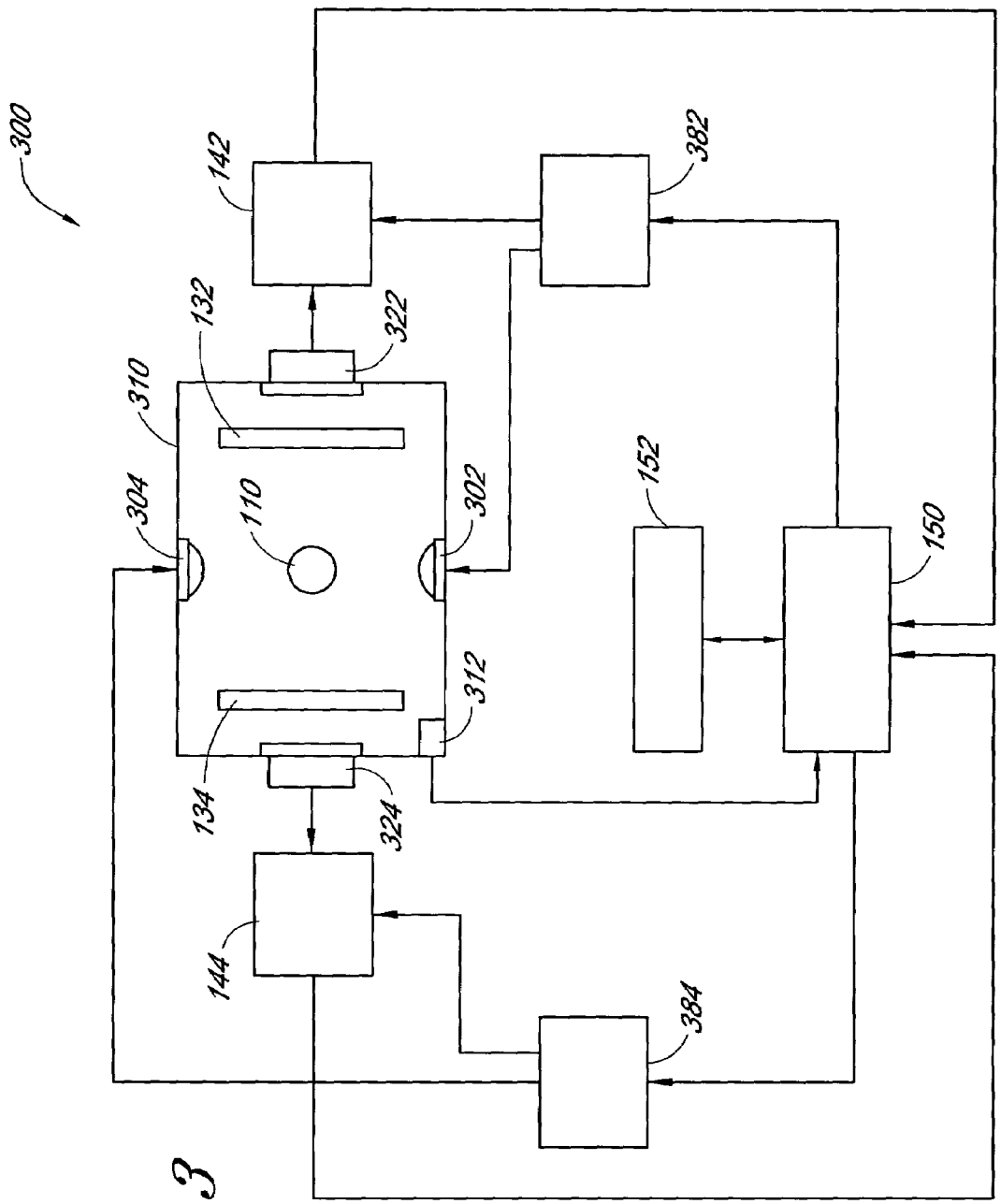
FIG. 3 is a functional block diagram of another embodiment of a ratio fluorometer.

FIG. 3 is a functional block diagram of another embodiment of a ratio fluorometer 300. The ratio fluorometer 300 of FIG. 3 is similar to the ratio fluorometer 200 of FIG. 2, except that two LEDs 302 and 304 are used as the excitation sources and photodiodes 322 and 324 are used as the detectors.

The support structure 310 is shown as a square, although the support structure 310 can have any shape that allows operation of the ratio fluorometer 300. A top view of the support structure 310 is shown in FIG. 3. A sample receptacle 110 is positioned in substantially the center of the support structure 310. A first LED 302 is placed on a first side of the support structure 310 and a second LED 304 is positioned on a second side of the support structure 310 opposite the side having the first LED 302.

A first filter 132 is positioned at substantially 90 degrees from the LEDs 302 and 304 and a first photodiode 322 is positioned along a third side of the support structure 310 to receive the signal passing through the first filter 132. A second filter 134 is positioned at substantially 90 degrees from the LEDs 302 and 304. The second filter 134 is positioned on a side of the sample receptacle 110 opposite the first filter 132. A second photodiode 324 is positioned along a fourth side of the support structure 310 to receive the signal passing through the second filter 324.

The output of the first photodiode 322 is coupled to a first ADC 142 where the signal is converted to a digital representation. The output of the first ADC 142 is coupled to the processor 150. Similarly, the output from the second photodiode 324 is coupled to a second ADC 144. The digital output from the second ADC 144 is coupled to the processor 150.

The processor 150 also controls a first control module 382 and a second control module 384. The first control module 382 controls the illumination from the first LED 302 and the conversion process of the first ADC 142. Similarly, the second control module 384 controls the illumination of the second LED 304 and the conversion process of the second ADC 144.

The first and second LEDs 302 and 304 can be Nichia LEDs having a maximum intensity at 375 nm. The first and second filters 132 and 134 are emission filters that are centered at 457 nm and 550 nm as was the case for the ratio fluorometer 200 of FIG. 2.

A temperature sensor 312 can be positioned near the sample receptacle 110. For example, the temperature sensor 312 can be positioned in the support structure 310. The temperature sensor 312 is configured to provide a temperature value, such as a voltage, current, value, or reading that corresponds to the temperature of the sensor. The processor 150 is also coupled to the temperature sensor 312 and can adjust the ratios or concentrations based, in part, on the temperature value received from the temperature sensor 312.

In this embodiment one of the LEDs, for example 302, is activated and fluorescence emitted at 90° is detected by one of the photodiodes, for example 322, by sampling the output multiple times over a predetermined period of time, for example, a period of 5 seconds. The fluorescence intensity for this photodiode 322 is determined from the average of the multiple samples. This is repeated for the second LED 304 and second photodiode 324. The ratio is computed from the fluorescence intensities from each photodiode and the same algorithm as used with the ratio fluorometer 200 of FIG. 2 is used to calculate the concentration of FFAu.

In this embodiment the two fluorescent intensities are obtained independently. In effect the ratio fluorometer 300 consists of two independent fluorometers, each with independent light sources, and detectors. Nevertheless, the stability of these two fluorometers relative to one another is sufficient to achieve a precision for determination of the ratio of on the order of 1%. This was determined from the coefficient of variation of 1% for repeated Ro measurements with a 1 $\mu$M ADIFAB2 solution at room temperature. This corresponds to an uncertainty in the determination of $[FFA_u]$ of approximately 0.4 nM for $[FFA_u]$ less than about 5 nM.

Figure 4:
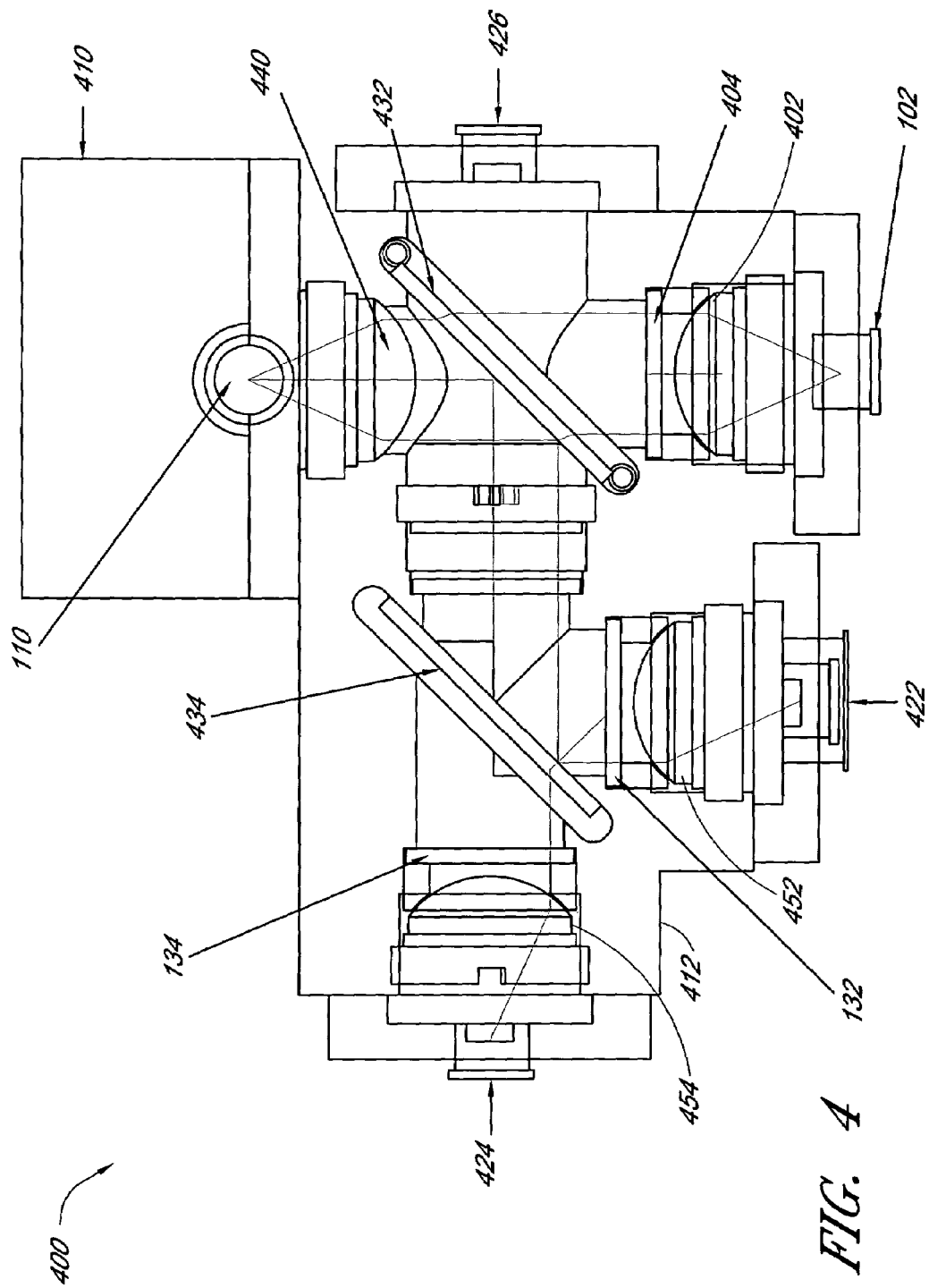
FIG. 4 is a functional block diagram of the optical portion of another embodiment of a ratio fluorometer.

FIG. 4 is a functional block diagram of the optical section of another embodiment of a ratio fluorometer 400. FIG. 4 shows only the optical section. The structure of ADCs and subsequent signal processing is similar to the previous embodiments.

A single LED light source 102 and three photodiode detectors 422, 424, and 426 are configured with epifluorescence/confocal optics. A ratio fluorometer is configured by combining the optical section 400 with appropriate signal processing electronics and software as previously described. The resultant ratio fluorometer can determine the ratio of fluorescence intensities with a coefficient of variation of less than 0.3%.

Excitation energy, or light from the LED 102 is focused on the sample receptacle 110. Light from the LED 102 passes through a excitation lens 402, an excitation filter 404, a first dichroic mirror 432 and is focused by a first lens 440 onto sample placed in the sample receptacle 110. The first dichroic mirror 432 is configured to substantially reflect light with wavelengths longer than a predetermined wavelength and substantially transmits light with wavelengths shorter than the predetermined wavelength. The first dichroic mirror 432, alternatively referred to as a dichromatic mirror, can be a 400 nm dichroic mirror. The 400 nm dichroic mirror thus substantially passes light having a wavelength shorter than 400 nm and reflects light having a wavelength longer than 400 nm. The sample receptacle 110 can be, for example, a cylindrical cuvette of about 4.5 mm inner diameter supported in a sample holder 410.

Emitted light is also collected through the first lens 440. A portion of the exciting light is reflected by the first 400 nm dichroic mirror into a reference photo diode 426, the output of which is used to normalize the outputs of the two emission photodiodes 422 and 424. Normalization eliminates effects due to intensity fluctuations of the LED 102. The fluorescence from the sample is reflected from the 400 nm dichroic mirror 432 to a second dichroic mirror 434. The second dichroic mirror 434 can be a 500 m dichroic mirror that passes light with wavelengths longer than 500 nm and reflects light with wavelengths shorter than 500 nm. Light reflected by the second dichroic mirror 434 is filtered by a first emission filter 132. The first emission filter 132 can be a 457 nm filter. The filtered output from the first filter 132 is provided to a first emission lens 452 that focuses the filtered emission onto a first photodiode 422. The remaining fluorescence is transmitted through the 500 nm dichroic mirror 434 to a second emission filter 134. The second emission filter 134 can be a 550 nm emission filter. Light passing through the second emission filter 424 is provided to a second emission lens 454 that focuses the filtered emission on a second photodiode 424 that detects the filtered emission. The optics, LED 102, and photodiodes 426, 424, and 422 can be supported in a optical frame 412 to which the sample support 410 is attached.

Signal processing is performed using a configuration similar to that used in the previous embodiments. An ADC can be connected to each of the photodiodes to convert the signals to digital representations. A processor can then perform signal processing on the digitized signals, including, but not limited to, normalizing the emission photodiode values with the reference photodiode value and calculating the ratio of detected fluorescence at the two wavelengths in order to determine a concentration of a molecule or atom in the sample.

To determine the concentration of a molecule or atom in a sample the processor initiates a sequence of power pulses to the LED 102. Typically, 10 pulses of 200 mS duration are used. The light from the LED 102 excites the fluorescent molecules in the sample and light or fluorescence from the sample generated by virtue of excitation from the LED 102 is detected by the photodiodes 422 and 424. The outputs from the photodiodes 422 and 424 are sampled and digitized using ADCs and the outputs of the ADCs are provided to a processor. Alternatively, the ADCs may be integral with the processor. The processor may be any type of processor, such as a general purpose processor, a microcontroller, or a digital signal processor (DSP). The output from the reference photodiode 426 is also digitized and the digitized values from the two emission photodiodes 422 and 424 are divided by the digitized value from the reference photodiode 426 that monitors the LED 102 output. These digitized and normalized outputs from the two emission photodiodes 422 and 424 are provided to the processor. The processor determines ratios as described earlier and can determine concentrations, such as $FFA_u$ concentrations based at least in part on the calculated ratio.

Thus, an inexpensive ratio fluorometer, such as the ratio fluorometer 300 of FIG. 3 or the ratio fluorometer 400 of FIG. 4, can be configured to determine fluorescent ratios with high sensitivity and high accuracy. The ratio fluorometer, for example 400, can achieve a coefficient of variation of ratio measurements as low as 0.08%. Alternatively, the ratio fluorometer may have coefficients of variation of less than 0.1%, less than 0.2%, less than 0.3%, less than 0.4%, less than 0.5%, less than 0.6%, less than 0.7%, less than 0.8%, less than 0.9%, or less than 1.0%.

Figure 5:
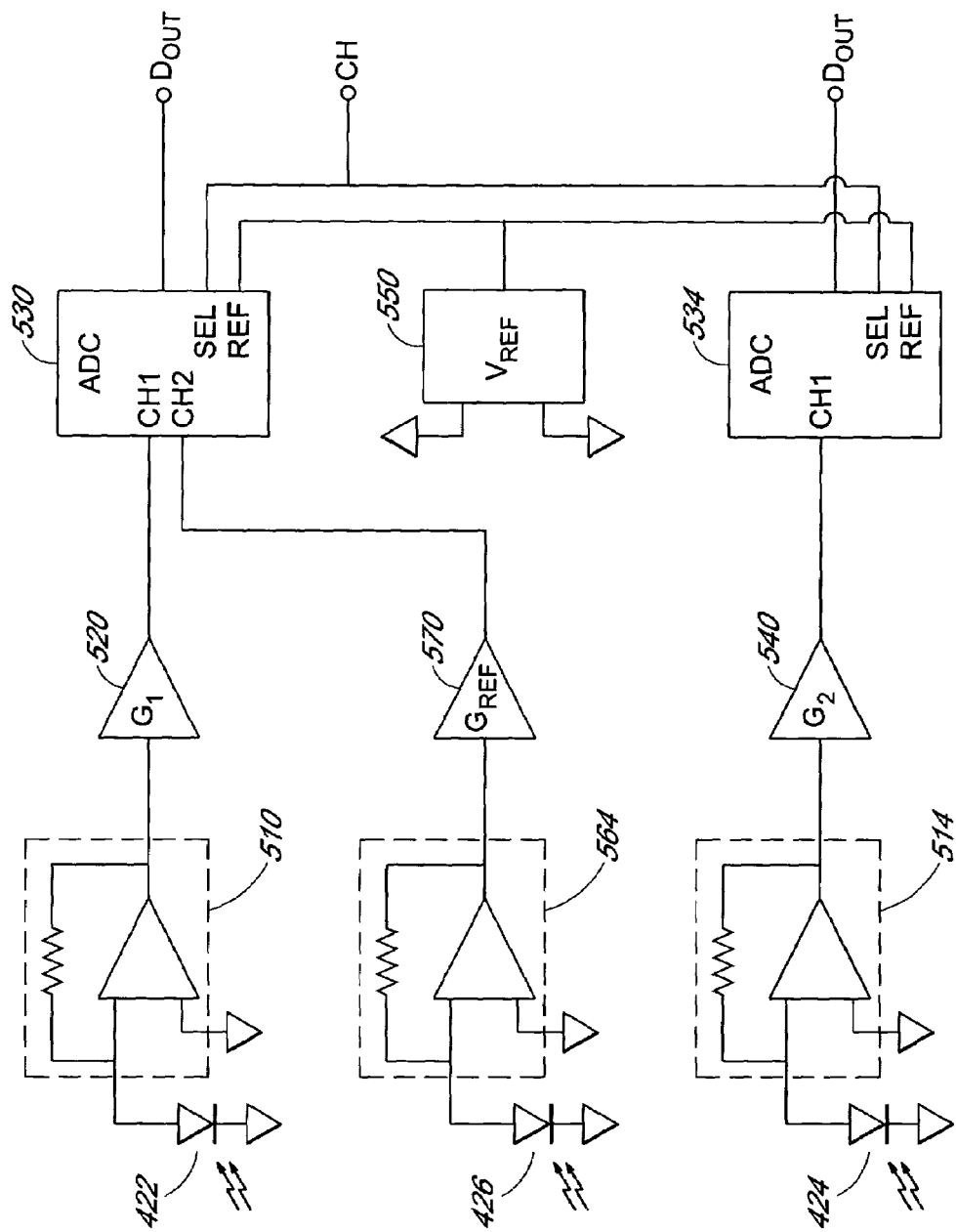
FIG. 5 is a functional block diagram of a signal processing section.

FIG. 5 is a functional block diagram of a signal processing section that can be used with the optical portion of FIG. 4. The signal processing section includes a reference photodiode 426 and first and second photodiodes 422 and 424. The signals from each of the photodiodes are amplified and converted to digital signals in one of two ADCs 530 and 534.

The signal processing section includes first and second photodiodes, 422 and 424, that are coupled to first and second transimpedance amplifiers, 510 and 514. The transimpedance amplifiers 510 and 514 provide a voltage output signal that is based on the current flowing through the respective photodiodes, 422 and 424. The output of the transimpedance amplifiers 510 and 514 are each coupled to an additional amplifier stage, 520 and 540 respectively. The amplifier stages 520 and 540 can also be configured as filters.

The output of the first transimpedance amplifier 510 is coupled to an input of a first amplifier 520, which can be, for example an operational amplifier (op amp) 520. The first amplifier 520 can have a fixed gain and frequency response or can have a configurable gain or frequency response. For example, the first amplifier 520 can use external components (not shown) to determine the gain and frequency response of the amplifier stage.

Similarly, the output of the second transimpedance amplifier 514 is coupled to an input of a second amplifier 540, which can be, for example, an op amp. The gain and frequency response of the second amplifier 540 can be fixed or configurable. The second amplifier 540 can use, for example, external components (not shown) to configure the gain or frequency response of the amplifier. The gain of the second amplifier 540 can be the same as, or different from, the gain of the first amplifier 520. The gain of the first and second amplifiers 520 and 540 can be positive. Alternatively, the gain of one or both of the first and second amplifiers 520 and 540 can be negative, denoting signal attenuation.

The outputs of the amplifiers 520 and 540 are coupled to corresponding ADCs 530 and 534. The output of the first amplifier 520 is coupled to a first input of a first ADC 530. Similarly, the output of the second amplifier 540 is coupled to the input of a second ADC 534. The ADCs 530 and 534 convert the analog signals into digital signals that are representations of the analog inputs. Having two ADCs 530 and 534 allows the photodiode signals corresponding to the sample emissions to be captured simultaneously. A precision voltage reference 550 is used as the voltage reference for both the first and second ADC 530 and 534.

The reference photodiode 426 is coupled to a transimpedance amplifier 564. The transimpedance amplifier can include, for example, an op amp having one or more feedback components that configure the gain and frequency response of the transimpedance amplifier. The output of the transimpedance amplifier 564 is also coupled to a reference gain stage 570 that can be configured similarly to the gain stages coupled to the first and second photodiodes 422 and 424. The output of the reference gain stage 570 is coupled to a second input of the first ADC 530. The first ADC 530 is configured to selectively convert the signal from the reference diode 426 or the first photodiode 422 based on a control signal from a processor or other control source (not shown).

Thus, in a first state, the signal processing section converts to a digital representation the signal from the reference diode 426 in the first ADC 530. In a second state, the signal processing section simultaneously converts to digital representations the signals from the first and second photodiodes 422 and 424. A subsequent processing section (not shown) can be configured to determine the ratios as described earlier.

Figure 6:
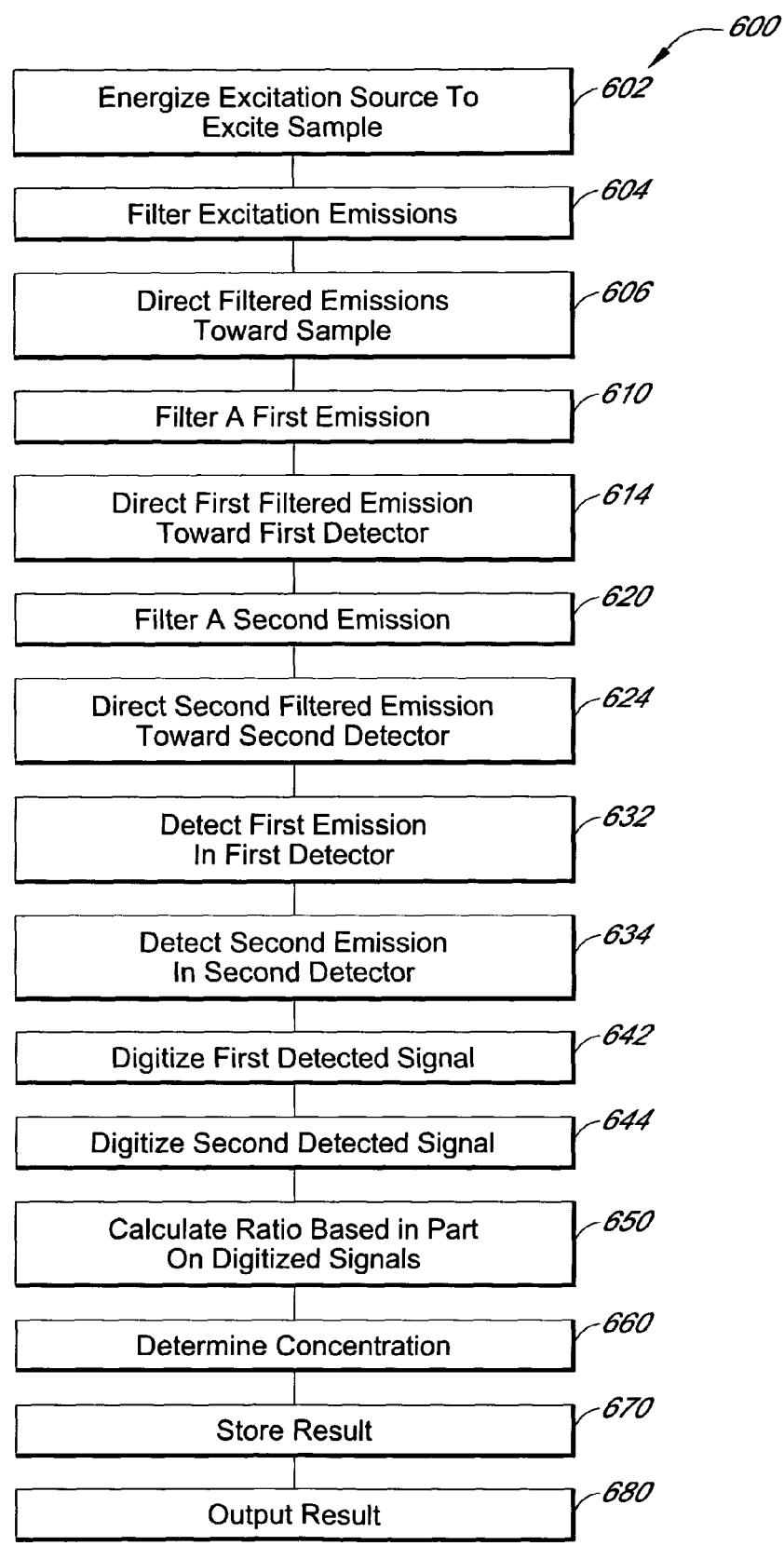
FIG. 6 is a flowchart of a method for determining the concentration of a sample using ratio fluorometry.

FIG. 6 is a flow chart of a method 600 of determining a target concentration in a sample using a ratio of detected fluorescent emissions. The method 600 assumes that blank intensities have been measured and stored in a location accessible by the ratio fluorometer and that a target sample is placed in a sample well of the ratio fluorometer.

The method 600 begins at block 602 where an excitation source is energized to excite the sample. At step 604 the ratio fluorometer filters the emissions from the excitation source. This step may be omitted when the excitation source is a narrowband source.

At step 606, the ratio fluorometer directs the filtered excitation emissions towards the sample. In the embodiments previously described, the filtered excitation emissions are directed towards the sample by the mechanical structure of the ratio fluorometer. However, the excitation emission may be directed using positioning mirrors, lenses, or mounts that may be controlled.

The ratio fluorometer then proceeds to block 610 where a first sample emission is filtered. As discussed above in the various embodiments, an optical filter can be used as a bandpass filter to pass those emissions centered about a first wavelength. The ratio fluorometer then proceeds to block 614 where the first filtered emission is directed towards a first detector. As was the case with the excitation emission, the first sample emission may be directed towards the first detector by mechanical, electrical, or optical means.

The ratio fluorometer proceeds to block 620 where a second sample emission is filtered. At block 624, the ratio fluorometer directs the filtered second emission to a second detector.

At block 632, the ratio fluorometer detects the first sample emission using the first detector. At block 634, the ratio fluorometer detects the second sample emission using the second detector.

The ratio fluorometer proceeds to block 642 where the first detected signal is digitized, for example, using a first ADC. At block 644, the second detected signal is digitized using, for example, a second ADC.

At block 650, the ratio fluorometer calculates a ratio based at least in part on the digitized signals. The ratio can also be base in part on the blank intensities that may be stored in memory. The ratio fluorometer can calculate the ratio in a processor running processor readable instructions stored in memory in the ratio fluorometer.

At block 660, the ratio fluorometer determines the concentration of the target based in part on the ratio calculated in block 644. At block 670 the ratio fluorometer stores the result in memory. At block 680 the ratio fluorometer outputs a result. The result may be, for example, a digital signal, meter value, display, graph, or numeric value.

Although the method 600 is organized as a sequential flowchart, one or more steps in the flowchart may be performed in a different order or may be performed concurrently with other steps in the method 600. For example, the excitation source may be energized concurrently with the filtering and directing of the excitation emissions and first and second sample emissions. Additionally, detecting the first sample emission may occur before, after, or concurrent with detecting the second sample emission. The first detected signal may be digitized before, after, or concurrent with digitizing of the second detected signal.

Although the order of many of the steps may be modified, typically the excitation sample is energized and the sample excited prior to detecting the first and second sample emissions. Additionally, the first and second sample emissions are typically detected prior to digitizing the detected emissions. However, the method 600 may run continuously and some detector outputs may be digitized prior to any sample being placed in the sample well. The ratio fluorometer may be modified such that only a subset of concentration values is stored and output. For example, the ratio fluorometer may receive a signal that initiates the concentration measurement and only those values determined within a predetermined time after receipt of the signal are stored and output. Other configurations are also within the scope of the ratio fluorometer.

In each of the embodiments described, machine or processor readable instructions or other software stored in memory control the processor functions. The processor readable instructions may direct the processor to perform various processes, including: a calibration step, a sample read step, a control read step, calculation steps, diagnostic functions, storage and transmission of results.

Additionally, the processor may comprise multiple processors. A first processor and memory may be located local to the optics and ADCs. A second processor and memory may be located remote from the optics and the first processor and memory. The processor may be distributed among two or more locations to minimize noise contributions and to allow for greater flexibility in the configuration of the ratio fluorometer.

For example, a first processor and memory can be located local to the optics, detectors, and ADCs. The first processor can control excitation and measurement of fluorescence from the sample. Additionally, the first processor can control calibration of the optics and detectors. Calibration coefficients and correction factors can be stored in the memory local to the first processor. The first processor can control the ADC sample timing and can format the digitized samples for transmission to the second processor.

The second processor can be, for example, a general purpose processor in a computer or personal computer. The first processor can transmit the digitized samples to the second processor using a communication link, such as an RS-232 link, an RS-422 link, a universal Serial bus (USB) link, an IEEE-488 link, an infrared link, a 4–20 mA current loop, a network link, a wireless link, and the like, or some other means for communicating data or information. The second processor can store the digitized samples in associated memory and perform the ratio calculations, concentration determination, and other signal processing on the digitized samples.

By distributing the processing across different pieces of hardware, the ratio fluorometer can be made to be portable and can have more flexible configurations. For example, the optics, detector, and first processor portions can be housed in a portable chassis and interface with a personal computer using a standard communication interface. Additionally, the optics, detectors, and first processor can be located remote from the personal computer such as in another room or across a laboratory.

Of course, the first processor is not limited to transmitting just the digitized samples. The first processor can be configured to perform some or all signal processing associated with the calculation of the ratios and the determination of the concentrations in the sample.

Although some of the embodiment descriptions refer to a first filter and a second filter, a ratio fluorometer is not limited to using two filters. The terminaology is used to identify functional blocks and may not necessarily refer to separate elements. In fact, the first filter and second filter may be the same filter. Additionally, a filter can comprise one or more filters. Similarly, some of the embodiment descriptions refer to first and second detectors, and first and second ADC. Again, the terminology is used for identification of functional blocks and does not imply that a ratio fluorometer is limited to having two of the identified devices.

The examples of instruments and methods of measuring FFA$_u$ with the ADIFAB2 molecule can readily be extended to other ratio and non-ratio molecules sensitive to fluorescent binding reagents and to other ligands. For example fluorescent molecules can be found that produce a change in a fluorescent ratio upon binding $Ca^{++}$, $Mg^{++}$, $K^+$, $Na^+$, etc. and thereby allow the concentration of these ligands to be determined. Non-ratio molecules used in conjunction with a reference fluorophore can be used to determine the ratios, and thus the concentrations, of other molecules.

Connections, couplings, and electrical connections have been described with respect to various devices or elements. The connections and couplings can be direct or indirect. A connection between a first and second device can be a direct connection or can be an indirect connection. An indirect connection can include interposed elements that can process the signals from the first device to the second device.

Those of skill in the art will understand that information and signals can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

Those of skill will further appreciate that the various illustrative logical blocks, modules, circuits, and algorithm steps described in connection with the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such the processor can read information from, and write information to, the storage medium. In the alternative, the storage medium can be integral to the processor. The processor and the storage medium can reside in an ASIC.

The above description of the disclosed embodiments is provided to enable any person skilled in the art to make or use the invention. Various modifications to these embodiments will be readily apparent to those skilled in the art, and the generic principles defined herein can be applied to other embodiments without departing from the spirit or scope of the invention. Thus, the invention is not intended to be limited to the embodiments shown herein but is to be accorded the widest scope consistent with the principles and novel features disclosed herein.

What is claimed is:

1. An apparatus comprising:
   a sample receptacle;
   an excitation source providing an excitation emission directed towards the sample receptacle;
   a first detector configured to detect a first sample emission;
   a second detector configured to detect a second sample emission, wherein an axis of the first sample emission is the same as an axis of the excitation emission; and
   a processor configured to calculate a ratio of the detected first sample emission to the detected second sample emission.

2. The apparatus of claim 1, further comprising a first filter interposed between the sample receptacle and the first detector and configured to substantially pass the first sample emission to the first detector.

3. The apparatus of claim 2, wherein the first filter comprises an optical filter.

4. The apparatus of claim 2, wherein the first filter comprises an optical filter having a passband of at least 420 nm to 460 nm.

5. The apparatus of claim 2, wherein the first filter comprises an optical filter having a passband of at least 430 nm to 490 nm.

6. The apparatus of claim 2, wherein the first filter comprises an optical filter having a pass band substantially centered at 457 nm and having a bandwidth of at least 10 nm.

7. The apparatus of claim 2, wherein the first filter comprises an optical filter having a pass band substantially centered at 457 nm and having a bandwidth of at least 20 nm.

8. The apparatus of claim 2, further comprising a second filter interposed between the sample receptacle and the second detector and configured to substantially pass the second sample emission to the second detector.

9. The apparatus of claim 8, wherein the second filter comprises an optical filter.

10. The apparatus of claim 8, wherein the second filter comprises an optical filter having a passband of at least 480 nm to 520 nm.

11. The apparatus of claim 8, wherein the second filter comprises an optical filter having a passband of at least 500 nm to 580 nm.

12. The apparatus of claim 8, wherein the second filter comprises an optical filter having a pass band substantially centered at 550 nm and having a bandwidth of at least 10 nm.

13. The apparatus of claim 8, wherein the second filter comprises an optical filter having a pass band substantially centered at 550 nm and having a bandwidth of at least 20 nm.

14. The apparatus of claim 1, further comprising an excitation filter interposed between the excitation source and the sample receptacle and configured to substantially pass the excitation emission.

15. The apparatus of claim 14, wherein the excitation filter comprises an optical filter.

16. The apparatus of claim 14, wherein the excitation filter comprises an optical filter having a passband of at least 350 nm to 400 nm.

17. The apparatus of claim 1, wherein the excitation source comprises a broadband light source.

18. The apparatus of claim 1, wherein the excitation source comprises a xenon light source.

19. The apparatus of claim 1, wherein the excitation source comprises a narrowband light source.

20. The apparatus of claim 1, wherein the excitation source comprises a Light Emitting Diode (LED).

21. The apparatus of claim 1, further comprising a first lens configured to collect the first sample emission onto the first detector.

22. The apparatus of claim 21, further comprising a second lens configured to collect the second sample emission onto the second detector.

23. The apparatus of claim 1, further comprising:
a first Analog to Digital Converter (ADC) configured to digitize an output from the first detector;
a second ADC configured to digitize an output from the second detector; and
wherein the processor calculates the ratio of the detected first sample emission to the detected second sample emission based, at least in part, on outputs from the first and second ADCs.

24. The apparatus of claim 1, further comprising a memory and wherein the processor stores the ratio of the detected first sample emission to the detected second sample emission in the memory.

25. The apparatus of claim 1, further comprising an output device and wherein the processor communicates the ratio of the detected first sample emission to the detected second sample emission to the output device.

26. The apparatus of claim 25, wherein the output device comprises a display.

27. The apparatus of claim 25, wherein the output device comprises a printer.

28. The apparatus of claim 25, wherein the output device comprises a computer.

29. The apparatus of claim 1, wherein the processor is further configured to determine a concentration of a molecule in a sample based, at least in part, on the ratio of the detected first sample emission to the detected second sample emission.

30. The apparatus of claim 29, wherein the concentration comprises a concentration of unbound free fatty acids.

31. The apparatus of claim 1, wherein the first detector comprises an optical detector.

32. The apparatus of claim 1, wherein the first detector comprises a photomultiplier tube.

33. The apparatus of claim 1, wherein the first detector comprises a photodiode.

34. The apparatus of claim 1, wherein the first detector comprises a Charge Coupled Device (CCD).

35. The apparatus of claim 1, wherein the first detector is positioned on an axis different from an axis of the excitation emission.

36. The apparatus of claim 1, wherein the first sample emission comprises a fluorescence from a molecule in a bound state and the second sample emission comprises a fluorescence from the molecule in a free state.

37. The apparatus of claim 1, wherein the first sample emission comprises a fluorescence from a first molecule whose fluorescence changes upon binding with a desired molecule and the second sample emission comprises a fluorescence from a second molecule whose fluorescence does not significantly change in the presence of the desired molecule.

38. A ratio fluorometer for determining a concentration of a target molecule in a sample, the fluorometer comprising:
a sample receptacle configured to support the sample;
an excitation light source directed towards the sample receptacle and configured to generate an excitation emission, wherein an axis of the excitation emission is the same as an axis of a first fluorescence from the sample;
a first optical filter configured to filter the first fluorescence from the sample;
a first detector configured to detect an output of the first optical filter;
a first Analog to Digital Converter (ADC) configured to generate a digital representation of an output of the first detector;
a second optical filter configured to filter a second fluorescence from the sample;
a second detector configured to detect an output from the second optical filter;
a second ADC configured to generate a digital representation of an output of the second detector; and
a processor configured to calculate a ratio, based in part, on the digital representations of the output of the first detector and the output of the second detector and to determine a concentration of the target molecule based, at least in part, on the ratio.

39. The fluorometer of claim 38, wherein:
the excitation light source comprises a light source having emissions with wavelengths of 350 nm–400 nm;
the first filter comprises a passband of 420 nm–460 nm; and
the second filter comprises a passband of 480 nm–520 nm.

40. The fluorometer of claim 38, wherein:
the excitation light source comprises a light source having emissions with wavelengths of 350 nm–400 nm;
the first filter comprises a passband of 430 nm–490 nm; and
the second filter comprises a passband of 500 nm–580 nm.

41. The fluorometer of claim 38, wherein:
the first filter comprises a passband configured to pass a fluorescence of ADIFAB2 when ADTFAB2 is bound to the target molecule; and
the second filter comprises a passband configured to pass a fluorescence of ADIFAB2 when ADIFAB2 is not bound to the target molecule.

42. The fluorometer of claim 38, wherein:
the first filter comprises a passband configured to pass a fluorescence of ADIFAB when ADIFAB is bound to the target molecule; and
the second filter comprises a passband configured to pass a fluorescence of ADIFAB when ADIFAB is not bound to the target molecule.

43. A ratio fluorometer for determining a concentration of unbound free fatty acids (FFAu) in a sample, the fluorometer comprising:
a sample receptacle configured to support the sample;
an excitation source configured to generate an excitation emission, wherein an axis of the excitation emission is the same as an axis of a first sample emission;
a first detector configured to detect a first fluorescence of a molecule when the molecule is bound to a ligand of the free fatty acid in the sample;
a second detector configured to detect a second fluorescence of the molecule when the molecule is unbound to the ligand of the free fatty acid in the sample; and
a processor configured to calculate a ratio, based at least in part, on an output of the first detector and an output of the second detector, and based at least in part on the ratio, to determine the FFAu concentration in the sample.

44. The fluorometer of claim 43, wherein the molecule comprises ADIFAB.

45. The fluorometer of claim 43, wherein the molecule comprises ADIFAB2.

46. A method comprising:
exciting a sample with an excitation emission;
detecting a first emission from the sample to produce a first detected emission, wherein an axis of the first sample emission is the same as an axis of the excitation emission;
detecting a second emission from the sample to produce a second detected emission; and
determining a concentration of a molecule in the sample based at least in part on the ratio of the detected emissions.

47. The method of claim 46, wherein exciting the sample comprises directing a light source having emissions in a 350 nm–400 nm wavelength band towards the sample.

48. The method of claim 46, wherein detecting the first emission from the sample comprises:
filtering an emission from the sample using a first optical filter;
detecting an output of the first optical filter to produce a first detector output; and
converting the first detector output to a first digital representation.

49. The method of claim 48, wherein filtering the emission from the sample comprises optically filtering the emission with a filter passband including 420 nm–460 nm.

50. The method of claim 48, wherein filtering the emission from the sample comprises optically filtering the emission with a filter passband including 430 nm–490 nm.

51. The method of claim 48, wherein filtering the emission from the sample comprises optically filtering the emission with a filter passband centered approximately at 457 nm.

52. The method of claim 48, wherein detecting the second emission from the sample comprises:
filtering the emission from the sample using a second optical filter;
detecting an output of the second optical filter to produce a second detector output; and
converting the second detector output to a second digital representation.

53. The method of claim 52, wherein filtering the emission from the sample comprises optically filtering the emission with a filter passband including 480 nm–520 nm.

54. The method of claim 48, wherein filtering the emission from the sample comprises optically filtering the emission with a filter passband including 500 nm–580 nm.

55. The method of claim 48, wherein filtering the emission from the sample comprises optically filtering the emission with a filter passband centered approximately at 550 nm.

56. A method of determining a concentration of a target molecule in a sample, the method comprising:
exciting the sample with an excitation emission from an excitation light source;
detecting, using a first detector, a first fluorescence from the sample, wherein an axis of the first fluorescence is the same as an axis of the excitation emission;
converting an output of the first detector to a first digital representation;
detecting, using a second detector, a second fluorescence from the sample;
converting an output of the second detector to a second digital representation;
calculating a ratio based, at least in part, on the first digital representation and the second digital representation; and
determining the concentration of the target molecule based, at least in part, on the ratio.

57. The method of claim 56, wherein exciting the sample comprises directing a light source having an emission bandwidth of at least 350 nm–400 nm at the sample.

58. The method of claim 56, wherein:
detecting the first fluorescence from the sample comprises detecting an emission from the sample in a 420 nm–460 nm wavelength band; and
detecting the second fluorescence from the sample comprises detecting an emission from the sample in a 480 nm–520 nm wavelength band.

59. The method of claim 56, wherein:
detecting the first fluorescence from the sample comprises detecting an emission from the sample in a 430 nm–490 nm wavelength band; and
detecting the second fluorescence from the sample comprises detecting an emission from the sample in a 500 nm–580 nm wavelength band.

60. The method of claim 56, wherein:
detecting the first fluorescence from the sample comprises detecting a first emission from molecules bound to ligands; and
detecting the second fluorescence from the sample comprises detecting a second emission from the sample molecules not bound to ligands.

61. The method of claim 56, wherein:
detecting the first fluorescence from the sample comprises detecting a first emission from ADIFAB2 molecules bound to ligands in the sample; and
detecting the second fluorescence from the sample comprises detecting a second emission from ADIFAB2 molecules not bound to ligands in the sample.

62. A method of determining a concentration of unbound free fatty acids (FFAu) in a sample, the method comprising:
determining a fluorescence of bound molecules from the sample using a first detector and epifluorescence;
determining a fluorescence of unbound molecules from the sample using a second detector; and
determining the concentration of FFAu in the sample based, at least in part, on a ratio of the fluorescence of bound molecules to the fluorescence of unbound molecules.

63. A measurement apparatus comprising:
a means for receiving a sample;
a means for exciting the sample;
a first means for detecting first sample emissions and configured with epifluorescence;
a first means for generating a first digital output corresponding to an output from the first means for detecting;
a second means for detecting second sample emissions;
a second means for generating a second digital output corresponding to an output from the second means for detecting; and
a processor configured to determine a concentration of target molecules in the sample based, at least in part, on a ratio of the first digital output to the second digital output.

64. A measurement apparatus, comprising:
- a first means for filtering a sample emission to produce a first filtered emissions, wherein the measurement apparatus is configured with epifluorescence;
- a first means for detecting the first filtered emission and producing a first detected emission value;
- a second means for filtering the sample emission to produce a second filtered emission;
- a second means for detecting the second filtered emission and producing a second detected emission value; and
- a processor coupled to the first means for detecting and the second means for detecting and configured to determine, based in part on a ratio of the first detected emission value to the second detected emission value, a concentration value.

65. The measurement apparatus of claim 64, wherein the first means for detecting and the second means for detecting comprise a single broadband detector.

66. The measurement apparatus of claim 65, wherein the first means for filtering and second means for filtering are successively placed in front of the single broadband detector.

67. The measurement apparatus of claim 64, wherein the processor in combination with the first means for detecting and second means for detecting determines the ratio of the first detected emission value to the second detected emission value with a coefficient of variation of less than 1.0%.

68. The measurement apparatus of claim 64, further comprising a temperature sensor configured to produce a temperature value, and wherein the processor determines the concentration value, based in part, on the temperature value.

69. A method of determining a concentration of a target molecule in a sample, the method comprising:
- detecting a first fluorescence from the sample in a first bandwidth to produce a first detected value, wherein the first fluorescence is detected using epifluorescence;
- detecting a second fluorescence from the sample in a second bandwidth to produce a second detected value;
- calculating a ratio based, at least in part, on the first detected value and the second detected value; and
- determining the concentration of the target molecule based, at least in part, on the ratio.

70. The method of claim 69, wherein the first bandwidth comprises a first interference absorbance bandwidth having a first optical density and the second bandwidth comprises a second interference absorbance bandwidth having a second optical density substantially equal to the first optical density.

71. The method of claim 69, wherein an optical density of an interference absorbance spectrum is substantially equal in the first and second bandwidths.

72. The method of claim 71, wherein the interference absorbance spectrum comprises a hemoglobin absorbance spectrum.

73. The method of claim 69, further comprising verifying an accuracy of the concentration of the target molecule.

74. The method of claim 73, wherein verifying the accuracy of the concentration of the target molecule comprises:
- preparing a control solution having a known concentration;
- determining a concentration of the control solution; and
- comparing the concentration of the control solution to the known concentration.

75. The method of claim 73, wherein verifying the accuracy of the concentration of the target molecule comprises:
- determining a concentration of a standard; and
- comparing the concentration of the standard to a predetermined concentration range.

76. The method of claim 75, wherein the standard comprises a solid standard including a solid fluorophore.

77. The method of claim 75, wherein the standard comprises a solution standard including a fluorophore in a defined solution.

78. A method of calibrating a ratio fluorometer; the method comprising:
- determining in a calibrating ratio fluorometer a ratio of fluorescence of a sample;
- determining in a second ratio fluorometer an uncorrected ratio of fluorescence of the sample; and
- adjusting a detector output such that the uncorrected ratio of fluorescence is substantially equal to the ratio of fluorescence.

79. The method of claim 78, wherein determining the ratio of fluorescence of the sample comprises determining a ratio of a fluorescent molecule in the presence of substantially no target molecules.

80. The method of claim 78, wherein determining the ratio of fluorescence of the sample comprises determining a ratio of an ADIFAB sample that is substantially devoid of free fatty acids.

* * * * *